US006329156B1

(12) United States Patent
Cirino et al.

(10) Patent No.: US 6,329,156 B1
(45) Date of Patent: Dec. 11, 2001

(54) METHOD FOR SCREENING INHIBITORS OF THE TOXICITY OF *BACILLUS ANTHRACIS*

(75) Inventors: Nick M. Cirino; Paul J. Jackson; Bruce E. Lehnert, all of Los Alamos, NM (US)

(73) Assignee: The Regents of the University of California, Los Alamos, NM (US)

(*) Notice: Subject to any disclaimer, the term of this patent is extended or adjusted under 35 U.S.C. 154(b) by 0 days.

(21) Appl. No.: 09/273,839

(22) Filed: Mar. 22, 1999

(51) Int. Cl.[7] .................... G01N 33/567; G01N 33/554; G01N 33/532; G01N 33/533
(52) U.S. Cl. ..................... 435/7.21; 435/7.32; 435/6; 435/4; 435/7.2; 436/544; 436/546; 436/172
(58) Field of Search .................... 435/7.32, 7.21, 435/4, 6, 7.2; 436/172, 164, 800, 805, 546, 544, 543, 63, 503, 501

(56) References Cited

FOREIGN PATENT DOCUMENTS

WO 94/18332 * 8/1994 (WO).

OTHER PUBLICATIONS

Klevytska et al. In: Abstracts of the 99th General Meeting of the American Society for Microbiology, Chicago, Illinois, May 30–Jun. 3, abstract 1999.*

* cited by examiner

*Primary Examiner*—S. Devi
(74) *Attorney, Agent, or Firm*—Samuel M. Freund (57) ABSTRACT

The protective antigen (PA) of *Bacillus anthracis* is integral to the mechanism of anthrax poisoning. The cloning, expression and purification of a 32 kDa *B. anthracis* PA fragment (PA32) is described. This fragment has also been expressed as a fusion construct to stabilized green fluorescent protein (EGFP-PA32). Both proteins were capable of binding to specific cell surface receptors as determined by fluorescent microscopy and a flow cytometric assay. To confirm binding specificity in the flow cytometric assay, non-fluorescent PA83 or PA32 was used to competitively inhibit fluorescent EGFP-PA32 binding to cell receptors. This assay can be employed as a rapid screen for compounds which disrupts binding of PA to cells. Additionally, the high intracellular expression levels and ease of purification make this recombinant protein an attractive vaccine candidate or therapeutic treatment for anthrax poisoning.

3 Claims, 3 Drawing Sheets

METHOD FOR SCREENING INHIBITORS OF THE TOXICITY OF *BACILLUS ANTHRACIS*

FIELD OF THE INVENTION

The present invention relates generally to inhibiting anthrax toxicity and, more particularly, to the identification of human antibodies which bind to the protective antigen (PA83) of *Bacillus anthracis*, thereby disrupting cell receptor binding thereof. This invention was made with government support under Contract No. W-7405-ENG-363 awarded by the U.S. Department of Energy to The Regents of The University of California. The government has certain rights in the invention.

BACKGROUND OF THE INVENTION

Virulent *Bacillus anthracis* continues to represent a significant health threat, although the mechanism of anthrax intoxication is relatively well understood (See, e.g., "The Anthrax Toxin Complex" by S. H. Leppla, *Sourcebook of Bacterial Protein Toxins*, p. 277, J. E. Alouf (ed.), Academic Press, London (1991)). An 83 kDa form of protective antigen (PA83) is secreted from rapidly growing *B. anthracis* cells and binds to a specific, but as yet unidentified, host cell surface receptors (See, e.g., "Anthrax protective antigen interacts with a specific receptor on the surface of CHO-K1 cells," by V. Escuyer and R. J. Collier, Infect. Immun. 59, 3381 (1991)). Subsequent cleavage by membrane-bound furin, and/or a furin-like protease, possibly PACE4, releases an amino terminal 20 kDa PA83 fragment resulting in receptor-bound PA63. The newly exposed surface on PA63 contains a single, high-affinity binding site that is recognized by the amino-termini of both the lethal factor and edema factor components of the toxin complexes. Endocytosis of the receptor/toxin complex into acidic endosomes elicits a conformational change in PA63, whereby the A subunits (LF or EF) of the toxin are released into the endosome. The PA63/receptor complexes then oligomerize into a heptameric ring. Lysosomal acidification and subsequent receptor release facilitate, irreversible membrane insertion of the oligomeric PA63 pore. The pore permits transport of LF and/or EF into the cytoplasm where they elicit their respective toxicities. EF is a calcium/calmodulin-dependent adenylate cyclase that is toxic to most cell types and causes local inflammation and edema, but is not usually lethal. LF is a cell-type specific metalloprotease that cleaves MAP-kinase-kinases and several peptide hormones. Lethal factor is the major virulence factor associated with anthrax toxicity and is responsible for systemic shock and death associated with a hyper-oxidative burst and cytokine release from macrophages. Neither of the toxin A subunits are pathogenic in the absence of cytoplasmic delivery by PA or mechanical means (See, "Macrophages are sensitive to anthrax lethal toxin through an acid-dependent process" by A. M. Friedlander J. Biol. Chem. 261, 7123 (1986)).

The crystal structures of PA83 and heptameric PA63 have been solved (See, e.g., "Crystal-structure of the anthrax toxin protective antigen" by C. Petosa et al., Nature. 385, 833 (1997)). These structural data support the experimental data (See, e.g., "Characterization of lethal factor-binding and cell-receptor binding domains of protective antigen of *Bacillus anthracis* using monoclonal-antibodies" by S. F. Little et al., Microbiology-UK. 142, 707 (1996) and "The carboxyl-terminal end of protective antigen is required for receptor-binding and anthrax toxin activity" by Y. Singh et al., J. Biol. Chem. 266,15493 (1991)) that indicate that domain 4, the carboxy-terminus of PA63, is responsible for receptor-mediated uptake of the toxin complex.

Phage display is a powerful tool with which moderate-to-high-affinity ligands can be rapidly isolated from diverse peptide or antibody libraries (See, e.g., "Making antibodies by phage display technology" by G. Winter et al., Ann. Rev. Immun. 12, 433 (1994)). Generation of naive antibody libraries, which are synthesized from non-immunized human rearranged V genes (See, e.g., "By-passing immunization: Human-antibodies from V-gene libraries displayed on phage" by J. D. Marks et al., J. Mol. Biol. 222, 581 (1991) and "Human-antibodies with sub-nanomolar affinities isolated from a large nonimmunized phage display library" by T. J. Vaughan et al., Nat. Biotech. 14, 309 (1996)), allows selection against a myriad of possible substrates. Isolation of antibody fragments from naive libraries has proven highly efficient against numerous targets, including viruses, cytokines, hormones, growth factor receptors and tissue or tumor specific markers. Phage display isolated single-chain Fv fragments ($scF_v$) have been used clinically for diagnostic imaging.

Previous investigations have shown that a vaccine containing only PA83 protected guinea pigs against lethal *B. anthracis* spore challenge, and PA-specific neutralizing monoclonal antibodies were able to delay the time of death. Such evidence suggests the possibility that high-affinity human antibodies generated against PA malt offer significant therapeutic advantage for humans as well.

The human anthrax vaccine used in the United States and other western countries consists of aluminum hydroxide-adsorbed supernatant material from cultures of toxigenic, non-encapsulated *B. anthracis* strains. Current protocols for isolating native PA83, the primary immunogen in the vaccine, from culture supernatants are time-and cost-intensive. Immunization with this vaccine can cause local edema and erythema, probably due to trace amounts of LF or EF, and frequent boosters arm required. It has been shown that only immunization with PA, but not LF or EF, can protect against lethal *B. anthracis* challenge in a guinea pig model.

It has been suggested that reduced protection seen with some recombinant PA vaccine preparations may be due to lack of contaminating LF or EF. Y. Singh et al. in "A deleted variant of *Bacillus anthrasis* protective antigen is non-toxic and blocks anthrax toxin action in vivo," J. Biol. Chem. 264, 19103 (1989) used recombinant PA molecules that bind receptors, but not LF or EF. Their approach was to mutate thie conserved PA83 RKKR protease site to prevent the EF/LF binding site from being exposed by furin cleavage and PA20 release. Immunization of guinea pigs with this cleavage-resistant PA vaccine led to significant protection against otherwise lethal anthrax infection (See, "Study of immunization against anthrax with the purified recombinant protective antigen of *Bacillus anthrasis* " by Y. Singh, Infect. Immun. 66, 3447 (1998)).

The use of natural and recombinant antibodies or antibody fragments to treat disease is at the forefront of many new therapeutics. A large proportion of new compounds in current clinical trials are human antibody derivatives. Indeed, the first phage display isolated antibodies (directed against tumor necrosis factor-α) are now being used as immunoglobulin therapeutics in phase II clinical trials for rheumatoid arthritis. There are many methods by which in vitro selection (i.e., separation of binding clones from non-binding clones) of displayed antibodies can be performed. These include biopanning of immobilized antigen on various substrates including plastic solid supports, columns, BIA-core chips, fixed cells, or even tissue sections.

Accordingly it is an object of the present invention to generate a recombinant PA fragment containing domain 4 to compete with native PA83 for its receptors, thereby inhibiting the first step required for toxin complex formation.

Another object of the invention is to generate a recombinant PA fragment to compete with native PA83 for its receptors which can be purified such that no anthrax toxin components remain after the manufacturing process.

Still another object of the invention is to provide a method for rapid screening for inhibitors of anthrax toxicity.

Yet another object of the present invention is to identify antibodies against domain 4 of PA83 as candidates for anthrax toxicity neutralization by interfering with PA83 binding to its host receptors.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for screening inhibitors of the toxicity for *Bacillus anthracis* hereof includes: generating the recombinant fragment PA32 from region 4 of PA83 of *Bacillus anthracis* and ligating the PA32 fragment to EGFP to produce EGFP-PA32; expressing the EGFP-PA32 to produce EGFP-PA32 protein; contacting the EGFP-PA32 protein with individual cells in a first sample of chosen cells, thereby generating a first sample of fluorescent cells; measuring the fluorescence from individual cells in the first sample of fluorescent cells; mixing EGFP-PA32 protein with a potential toxicity inhibitor for *Bacillus anthracis*; contacting the mixture of EGFP-PA32 protein and the potential toxicity inhibitor with individual cells in a second sample of chosen cells, forming thereby a second sample of fluorescent cells; measuring the fluorescence from individual cells in the second sample of fluorescent cells; and comparing the fluorescence from individual cells in the first sample of fluorescent cells with the fluorescence from individual cells in the second sample of fluorescent cells, whereby the effectiveness of the toxicity inhibitor is determined from the decrease of the fluorescence from individual cells from the second sample of fluorescent cells relative to the fluorescence from individual cells in the first sample of fluorescent cells.

Preferably, the chosen cells include A549 human bronchial epithelial cells.

It is also preferred that fluorescence from individual cells is measured using flow cytometry.

In another aspect of the present invention in accordance with its objects and purposes the method for inhibiting the toxicity of *Bacillus anthracis* hereof includes introducing the recombinant fragment PA32 protein into an exposed individual, whereby PA83 is competitively inhibited from binding to the cells of the exposed individual.

In yet another aspect of the present invention in accordance with its objects and purposes, the method for inhibiting the toxicity of *Bacillus anthracis* hereof include:; introducing human $scF_v$#4 protein into an exposed individual, whereby the $scF_v$#4 binds to PA83, thereby preventing PA83 from binding to the cells of the exposed individual.

In still another aspect of the present invention in accordance with its objects and purposes, the method for inhibiting the toxicity of *Bacillus anthracis* hereof includes introducing the recombinant fragment PA32 protein into an individual, whereby antibodies suitable for preventing PA83 from binding to the cells of the individual exposed to *Bacillus anthracis* are generated by the individual; that is, immunization occurs.

In a further aspect of the present invention in accordance with its objects and purposes, the method for inhibiting the toxicity of *Bacillus anthracis* hereof includes introducing DNA-encoding PA32 into the genetic material of host cells, whereby the host cell machinery transcribes and translates PA32 which secretes the recombinant, synthetic antibody fragment, thereby acting as a DNA vaccine.

In still a further aspect of the present invention in accordance with its objects and purposes, the method for inhibiting the toxicity of *Bacillus anthracis* hereof includes introducing DNA-encoding $scF_v$ into the genetic material of host cells, whereby the host cell machinery transcribes and translates $scF_v$ which secretes the recombinant, synthetic antibody fragment.

Benefits and advantages of the invention include a high-throughput screen for inhibitors of receptor binding of *Bacillus anthracis* PA83. The recombinant form of PA, PA32, generated according to the teachings of the present invention is safer to manufacture (i.e., no *B. anthracis* cultures necessary), simpler to purify, and has no chance of 'carrying' other toxin components through the manufacturing process. Dual vaccination with PA32 and LF or EF would be possible since the A toxin subunits cannot interact with recombinant PA32.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Briefly, the present invention includes the identification of human $scF_v$ as potential prophylactics or therapeutics against anthrax poisoning, and the use of recombinant PA32 as a potential prophylactic or therapeutic agent to compete with anthrax toxins for cellular receptors during active infection. A method for identifying antibodies that bind native *B. anthracis* protective antigen PA83 using a high-throughput flow cytometric competition assay has been developed. This assay employs a fluorescently tagged form of PA32, and a naive, human single-chain $F_v$ (scF$_v$) phagemid library has been investigated thereby. Certain scF$_v$ that bind to PA83 have been isolated by the present inventors using biopanding. The recombinant PA32 retains its ability to undergo receptor-mediated uptake and is also recognized by the scF$_v$ isolated by biopanning which recognized PA83. At least one scF$_v$ antibody fragment that blocks binding of the fluorescently tagged PA32 moiety to cell surface receptors has been identified. Selected scF$_v$ were first isolated from the naive library by biopanning against PA83. Soluble, monomeric scF$_v$ were then characterized for affinity and screened for their capacity to disrupt receptor mediated binding of PA. Four of the scFv were found to bind to PA83, as determined by surface plasmon resonance, the tightest binder exhibiting a $K_d$ of 50 nM. Two of these scFv displayed similar affinities for both natural PA83 and the 32 kDa carboxy-terminal PA fragment (PA32). Fusion of EGFP to PA32 facilitated development of the flowcytometric assay of the present invention that showed that one of the scFv actually disrupts PA receptor binding. The present method can now be used as a rapid assay for other small molecule inhibitors of PA binding to cell receptors.

Reference will now be made in detail to the present preferred embodiments of the present invention examples of which are illustrated in the accompanying drawings.

A. Cell Culture:

Chinese hamster ovary cells (CHO-K1, ATCC# C.CL-61) were cultured in minimal essential media (MEM) supplemented with 10% (vol./vol.) of fetal bovine serum (FBS), 100 U/ml penicillin and 100 μg/ml streptomycin. A549 human lung carcinoma, alveolar epithelial cells (ATCC# C.CL-185) were cultured in RPMI 1640 culture media supplemented with 10% FBS and the antibiotics mentioned above. Both cell types were released from culture flasks by incubation in 1 mM trypsin/EDTA for 3 min. at 37° C. Cells were washed once in phosphate-buffered saline (PBS) and diluted to $10^3$/ml in appropriate culture media for passage to new flasks. For immunofluorescent microscopy, cells were cultured on LABTEC2 slides. For flow cytometric assay, cells were released with trypsin/EDTA, washed once in culture media and once in PBS before subsequent treatments.

B. Protective Antigen and Edema Factor Cloning:

PCR using Pfu polymerase was carried out on a thermal cycler using an annealing temperature of 52° C. and an extension time of 5 min. The forward and reverse primers for PA32 (SEQ ID NO. 7) were:
FOR: 5'TCGCACTCGAGGGCGCGCATGCCGC-CGAAACAACTGCACGTATCATT (SEQ ID NO. 1)
REV: 5'ACTGAGCTCAGCGCTAGCGCCACCA-GAACCGCCTCCTATCTCATAGCCTTTTT (SEQ ID NO. 2)
(sequences complementary to PA83 are in italics). Template was *B. anthracis* Sterne strain pXO1. The amplified PCR product was 809 nucleotides long (PA sequence 3346–4095, Accession# M22586) and contained restriction sites for XhoI and BssHII at the 5' end and Bpu 1102I and NheI at the 3' end, respectively. PCR products were gel purified and cut with the appropriate enzyme pairs (i.e., XhoI and Bpu1102I) for ligation into pET15b (Novagen) expression vector. This vector adds a hexahistidine tag to the amino terminus of expressed proteins. DNA sequencing was performed to confirm the correct construction. The BssHII and NheI sites have no significance to the present invention. The pET15b-expressed protein contained the *B. anthracis* mature PA sequence from E486 to G735, which includes the experimentally defined PA receptor binding domain. These constructs were then transformed into *E. coli* strain BL21(DE3) pLysS (Stratagene). Bacteria were grown in Luria-Bertani (LB) broth supplemented with 50 μg/ml ampicillin and 34 μg/ml chloramphenicol. Induction by addition of 1.5 mM isopropyl-β-D-thiogalacto-pyranoside (IPTG) was performed at 37° C. for 4 h. Ten-to-20 mg of PA32 (SEQ ID NO. 8) was purified from cleared bacterial lysates from a 1 L mid-log phase shaker culture passed through a 2 ml Talon metal affinity resin column according to the manufacturer's protocol.

The sequence encoding the *B. anthracis* edema factor amino terminus (Accession# M23179) was cloned into pET15b generating EF32. PCR primers were:
FOR: 5'-GCTCGAGMTGAACATTACACTG (SEQ ID NO. 3)
REV: 5'-CGCTCAGCACCTTCTTTCTTCAAACTTTC (SEQ ID NO. 4)
They contained XhoI and Bpu1102I restriction sites, respectively (sequences complementary to native edema factor (EF89) are in italics). This edema factor fragment (amino acids N35 to G289) was cloned because the resultant EF fragment retains its ability to bind PA63, yet is enzymatically inactive.

C. EGFP-fusions Cloning:

The enhanced green fluorescent protein (EGFP) sequenc(e from Clontech was amplified with primers:
FOR: 5'-GGAATTCCATATGGTGAGCAAGGGCGAG GAGCTGTTCACC (SEQ ID NO. 5)
REV: 5'-CCGCTCGAGATCTGAGTACTTGTACAG CTCGTCCATGCC (SEQ ID NO. 6)
and ligated into pET15b/PA32 or pET15b/EF32 between the NdeI and XhoI sites. These chimeric constructs were transformed into *E. coli* BL21(DE3)pLysS. Bacteria expressing recombinant proteins were grown and induced as set forth hereinabove. Recombinant proteins were purified by IMAC as set forth hereinabove.

D. PA83 Isolation:

PA83 was purified as described in "Purification of anthrax-toxin components by high-performance anion-exchange; gel-filtration and hydrophobic-interaction chromatography" by C. P. Quinn et al., J. Biochem. 252, 753 (1988). Briefly, clarified supernatant was collected from a 20 L culture of pXO2 cured Sterne strain *B. anthracis* containing mutant LF and EF. A 20% ammonium sulfate precipitation was used to enrich PA83 relative to other secreted proteins. Subsequent FPLC purifications were performed using MONO-Q and gel filtration (SEPHADEX G-75) columns. The final protein preparation was >90% pure as determined by SDS-polyacrylamide gel electrophoresis.

E. scF$_v$ Display, Isolation, Purification, and Characterization:

A naive scFv phagemid library (6×10$^9$ diversity; see, "Efficient construction of a large non-immune phage antibody library: The production of high-affinity human single-chain antibodies to protein antigens" by M. D. Sheets et al., Proc. Natl. Acad. Sci. USA. 95, 6157 (1998)) was selected against PA83 following previous protocols (See, "Isolation of high-affinity monomeric human anti-c-erbB-2 single-chain $F_v$ using affinity-driven selection" by R. Schier et al., J. Molec. Biol. 255, 28 (1996)). Three rounds of biopanning were performed in NUNC IMMUNO-TUBES. Washing after each selection round consisted of 20 washes with PBS/TWEEN-20 (0.1% vol./vol.), followed by 20 washes with PBS. Phages were eluted with 100 mM triethylamine, pH 12, then neutralized with 1 M Tris-HCl, pH 7.4. Sandwich ELISAs were performed using 96 well plates coated with 1 µg PA83. Anti-M13lhorse radish peroxidase (HRP) conjugate was used for colorimetric detection with tetramethyl benzidine (TMB). Fingerprint analysis of PCR-amplified antibody variable ($F_v$) regions from ELISA-positive phage using BstNI restriction enzyme was used to identify unique isolates. Plasmids containing the isolated antibody clones were transformed into *E coli* BL21(DE3) pLysS and soluble antibody fragment production was induced by stimulation with 1.5 mM IPTG for 6 h at 30° C. A periplasmic preparation was produced as previously described and His-tagged $scF_v$ were isolated by immobilized metal affinity chromatography (IMAC). Monomeric $scF_v$ were isolated by size exclusion chromatography using SUPERDEX 75 as previously described.

F. Binding Analysis by Surface Plasmon Resonance:

All protein binding experiments were performed in a system which characterizes biomolecular interactions using surface plasmon resonance, SPR, which is a non-invasive optical detection technique. SPR reflects a change in mass concentration at the detector surface as molecules bind or dissociate. One component, the ligand, is covalently attached to a single channel of the flowcell surface. The other component, the analyte, is injected in a continuous flow over the flowcell surface. PA83, PA32, EGFP-PA32, and EGFP-EF32 were coupled to four different channels on a CM5 DEXTRAN sensor chip in 10 mM sodium acetate (pH 4.8) via the amine group of lysines using NHS-EDC chemistry. All ligands were coupled to less than 1000 resonance units (RU) per channel. Single-chain $F_v$ selected against PA83 were dialyzed extensively against PBS and passed over immobilized ligand at a flow rate of 40 µL/min. in PBS. Eighty µL of analyte was injected and run over successive channels of ligands in a single flowcell. Four concentrations, ranging from 2 to 100 nM of each analyte, were assessed and used for binding analysis. Curves were fit to a 1:1 stoichiometry of binding with mass transfer compensation. The flowcell was regenerated between samples using a 4 M $MgCl_2$ solution without significant change in baseline.

G. Immunofluorescent Microscopy:

Recombinant PA32 was covalently labeled with TEXAS-RED. Briefly, 1.5 mg TEXAS-RED-X succinimidyl ester was dissolved in 150 µL DMSO (final concentration of 12 mM). Four µL of this soluble dye were added to 50 µL of 100 µM PA32 giving a molar ratio of 10:1. Conjugation proceeded for 30 min. at 30° C. followed by 30 min. at 4° C. Unconjugated dye was removed by separation through a Microcon 10 column. CHO cells were cultured on LABTEK2 slides to 80% confluency. Cells were washed twice with cold MEM and stored at 4° C. until use. One mmol fluorescently labeled PA32 was added and the temperature was shifted to 37° C. for different time periods. Cells were then fixed in 100% methanol for 15 min., washed once in PBS, then covered with glycerol mounting media. PA32 labeling of the cells was photographed using a 60× oil immersion objective on a CCD camera-equipped AXIOSKOP model ZEISS microscope. A 100 watt Mercury lamp was used for excitation of fluorophores.

H. Flow Cytometry Assay:

Cells were diluted to $10^6$/ml and 10,000 events were collected. The forward scatter (FSC) detector was E-1 (gain 350), the side scatter (SSC) detector was set at 350 and green fluorescence detector (FL1) at 500 on a log scale. Cells were washed once in PBS, diluted to 106/ml in PBS containing 1.5% (weight/vol.) bovine serum albumin (BSA), and agitated for 2 h at 4° C. to block non-specific protein binding. One-half ml aliquots of cells were then dispensed into chilled 1.5 ml EPPENDORF tubes. EGFP or EGFP-fusion proteins in PBS were added to a 0.2 µM final concentration of and allowed to bind for 1 h at 4° C. with moderate agitation. Cells were centrifuged at 2000× g for three min. decanted, and resuspended in 1 ml PBS containing 0.1% BSA (weight/vol.), and analyzed. For competition experiments, non-fluorescent PA83 or PA32 was added to the cells prior to EGFP-PA32. For analysis of $scF_v$ inhibition, EGFP-PA32 was incubated with different antibody fragments for 2 h at 4° C. prior to addition to A549 cells.

Having generally described the invention, the following EXAMPLES provide additional details.

EXAMPLE 1

By selecting against purified PA83 on a solid plastic support which does not orient the bound protein, selection against all portions of PA83 is forced. Several unique, high affinity clones which were against different epitopes (as determined by the ability to bind the PA32 subdomain of PA83) were isolated. These scFv were used for western blots and immunoprecipitations (data not shown) and were screened for the potential to disrupt host cell receptor binding. Isolation of neutralizing scFv from naive libraries is less efficient than from immune libraries, yet a scFv which could inhibit receptor mediated binding of PA to cells was found. If the affinities of these $scF_v$s are not sufficiently high, their affinities can be increased by chain shuffling or parsimonious mutagenesis. Alternatively, scfv isolated from immune libraries have generally shown higher affinities.

A. SDS-PAGE Analysis of Purified Recombinant and Natural PA Proteins:

Purification of the native PA83 as described hereinabove yielded a >90% pure protein preparation. Purification of recombinant anthrax proteins was performed by immobilized metal affinity chromatography (IMAC) in a single step. All IMAC purified proteins were >95% homogeneous after elution as determined by SDS-polyacrylamide gel electrophoresis. A recombinant PA comprised of the carboxy-terminal 32 kDa is highly soluble in *E. coli* and did not appear to be toxic to the bacteria. PA32 was also cloned as a fusion protein with a green fluorescent protein variant (EGFP) attached to its amino terminus. The EGFP-PA32 fusion was designed for use in a flow cytometry assay where inhibitors of PA receptor binding could be analyzed. As controls for the different assays, His-tagged EGFP (full length 31 kDa), and chimeric EGFP-EF32 were expressed and purified similar to the recombinant PA32 proteins.

B. Characterization of Isolated $scF_v$:

Synthetic, recombinant, single-chain $F_v$ from a naive phage display library were biopanned against PA83. Following 3 rounds of selection, 60 of 90 isolates showed PA binding ability, as determined by ELISA (data not shown). Fingerprint analysis revealed 7 unique isolates, of which 5 with the highest ELISA scores were chosen for further analysis (TABLE). These $scF_v$ were expressed and purified by IMAC and size exclusion chromatography to isolate monomeric $scF_v$. This was necessary to assess the affinity of the antibodies in the absence of avidity effects due to diabody or larger aggregate formation (e.g. one of the antibody fragments, scF$_v$#5, showed >90% multimerization and was therefore excluded from subsequent analysis (TABLE). This procedure yielded >95% pure antibodies as determined by SDS-PAGE.

TABLE

Analysis of anti-PA83 selected single-chain F$_v$.

| | ELISA[a] | Mono/Di/Trimer[b] | Kd (M)[c] | |
|---|---|---|---|---|
| ScF$_v$#1 | 0.75 | 8:2:0 | 1.9 × 10$^{-1}$ | SEQ. ID No. 9 |
| ScF$_v$#4 | 0.20 | 9:1:0 | 3.1 × 10$^{-1}$ | SEQ. ID No. 10 |
| ScF$_v$#5 | 1.14 | 1:2:7 | ND[d] | |
| ScF$_v$#12 | 0.27 | 7:3:0 | 1.1 × 10$^{-6}$ | SEQ. ID No. 11 |
| ScFv#24 | 0.30 | 9:1:0 | 4.3 × 10$^{-1}$ | SEQ. ID No. 12 |

Wells of 96 well plate coated with 1 μg PA83. Anti-M13-HRP conjugated antibody was used to generate signal. eMultimer content was determined by SEPHADEX-75 separation of IMAC purified protein as described hereinabove. Affinity was determined using 4 concentrations of each scF$_v$ by BIACORE. ND, not done.

Figure 1:
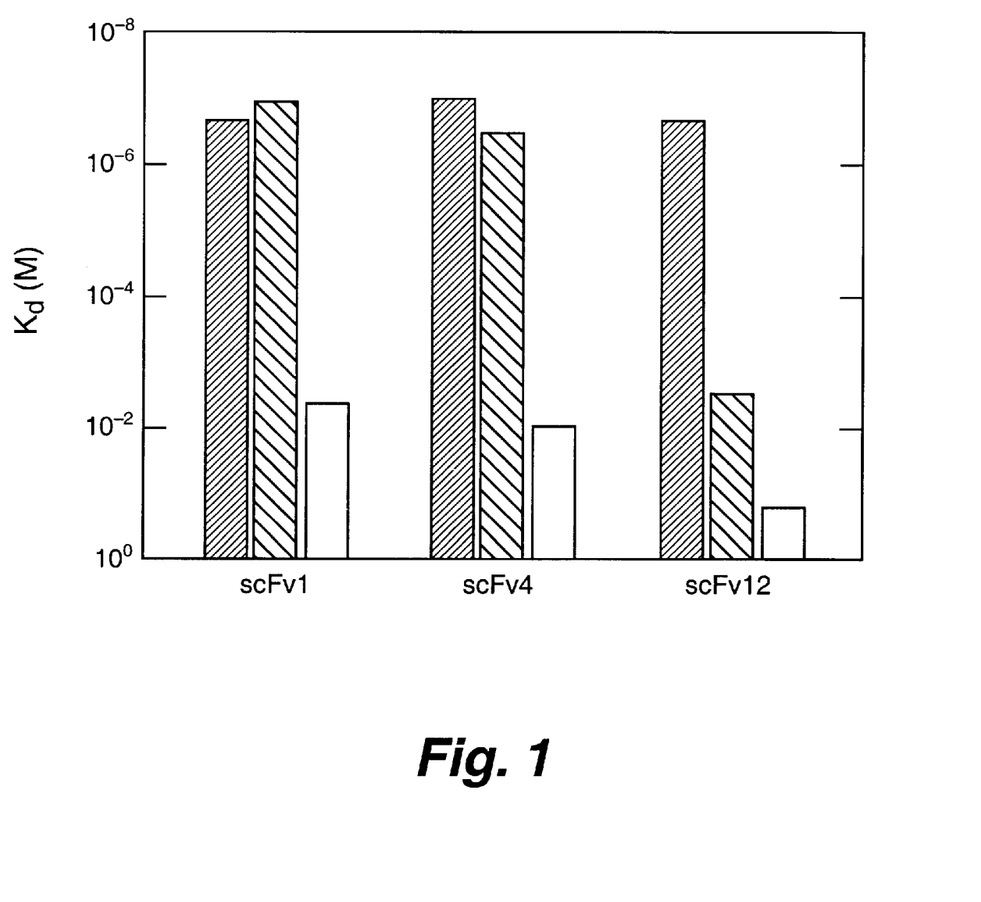
FIG. 1 shows the affinities of anti-PA83-selected, single-chain $F_v$ determined by surface plasmon resonance, black bars indicating the affinities of selected $scF_v$ for natural PA83, striped bars indicating affinities for recombinant EGFP-PA32, and white bars indicating affinities for recombinant EGFP-EF32.

C. Characterization of scFv Binding Affinities to PA:

PA83 was coupled to a BIAcore CM5 chip (~1000 RU) and four dilutions of each of the purified, monomeric scF$_v$ were used to determine equilibrium dissociation constants (K$_d$). All scF$_v$ tested showed similar affinities (TABLE). The overall affinities of these antibody fragments are consistent with models that predict sub-micromolar affinities for naive libraries of this size. These scF$_v$ were further assessed for their ability to recognize the recombinant PA32 fragment. PA83, EGFP-PA32, PA32, and EGFP-EF32 were coupled to different channels on a single BIAcore CM5 flowcell. Different scF$_v$ were sequentially passed over each channel of the chip and their affinity determined (FIG. 1). All ligands were coupled at ~1000 RU and a single concentration of analyte was assessed. There is good agreement in K$_d$ for the different scF$_v$ binding to PA83 comparing TABLE and FIG. 1. K$_d$ less than 10$^{-7}$ M were apparent for all three antibodies directed against PA83. Baseline, nonspecific binding was evident in all three scFv (K$_d$~10$^{-2}$ M) passed over nontarget EGFP-EF32. Two scF$_v$s (#1 and #4) showed similar affinities for PA83 and PA32 ligands while scF$_v$#12 showed only non-specific binding to PA32 proteins (FIG. 1). These data indicate that the targets for scF$_v$#1 and scF$_v$#4 lie within domains 3 or 4 of PA while the antigenic site for scFv12 is outside this region.

D. Confirmation of PA32 Cell Binding and Internalization:

The above SPR data suggested that the expressed PA32 fragment was correctly folded, at least in terms of epitope presentation, and could be used as a reporter to monitor PA-receptor interaction. Purified, recombinant PA32 was covalently cross-linked to the fluorophore, TEXAS-RED. This fluorescent-PA32 was added to serum-deficient CHO cell cultures. Receptor internalization was induced by shift in temperature from 4° C. to 37° C. for different times. There was a time-dependent internalization of fluorescence into discreet structures, presumably endosomes, within the cytoplasm of these cells. No fluorophore internalization was seen if the cells were kept at 4° C. and fluorescent label was not observed in nuclei, even at 6 h post-temperature release (data not shown). These data indicate that the PA32 fragment is recognized similar to natural PA83 and internalized into cytoplasmic vesicles.

Preliminary work by S. H. Leppla in "Production and purification of anthrax toxin," Meth. Enz. 165, 103 (1988) to generate a recombinant carboxyl-terminal PA fragment indicated a fragment from T624-G735 could not compete with radio-labeled PA83 for receptors. This work was completed prior to the crystal structure solution. It is believed by the present inventors that the reason PA32 (domains 3 and 4) is able to compete for receptors is that the protein is structurally more stable than the T624-G735 fragment tested by Leppla and co-workers. This hypothesis is supported by the present SPR results that show several of the anti-PA83 scF$_v$ also bind to PA32; that is, the molecule evidently is folded in a manner that preserves epitopes common to native PA. The ability of PA32 to interact with its host cell surface receptor (FIG. 2) and be internalized favorably supports the possibility that this PA fragment may be effective as an anti-toxin treatment during anthrax infection.

EXAMPLE 2

Figure 2:
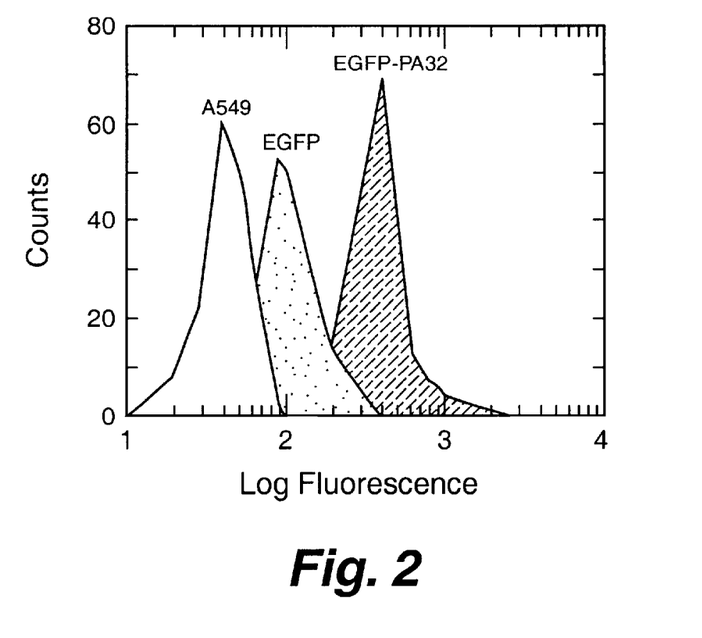
FIG. 2 shows the flow cytometric analysis of specific EGFP-PA32 binding bit the A549 human epithelial cell line, where the number of cells is illustrated on the ordinate and the log of fluorescence intensity on the abscissa, the green fluorescence signal from non-labeled cells being shown in black, the non-specifically labeled EGFP being shown by the striped curve, and the specific labeling of EGFP-PA32 being shown in white.
Figure 3:
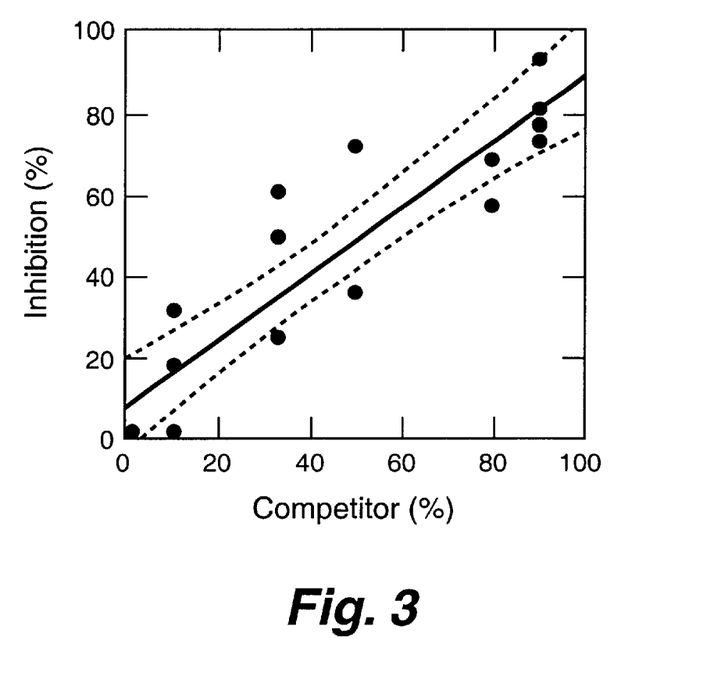
FIG. 3 shows the flow cytometric analysis of the inhibition of EGFP-PA32 signal by unlabelled PA, the 95% confidence interval being shown by the dotted line.

A. Rapid Flow Assay to Assess PA32/receptor Interactions:

A flow cytometric assay was developed using the EGFP-PA32 fusion protein. Human A549 cells were used as target cells because of their low autofluorescence and minimal phagocytic activity. EGFP alone or the EGFP-EF32 fusion was used to evaluate nonspecific binding by these cells. Initial experiments were performed to ensure significant separation of non-specific and receptor-mediated protein binding. As shown in FIG. 2, there was a 4-fold enhanced signal from specific EGFP-PA32 bound to cells compared to non-specific EGFP binding alone. To confirm that EGFP-PA32 was binding to the PA specific receptor, competition with different concentrations of natural PA83 or unlabelled PA32 was assessed. There was a statistically significant (p<0.0001) linear inhibition of fluorescent-PA32 binding by unlabeled PA molecules (FIG. 3). For a 1:1 stoichiometry of PA/receptor binding, a 50% inhibition by an equimolar concentration of unlabelled PA would be expected (i.e. 50% EGFP-PA32, 50% competitor). This data confirms specificity and indicates little or no cooperativity in PA/receptor interactions.

Figure 4:
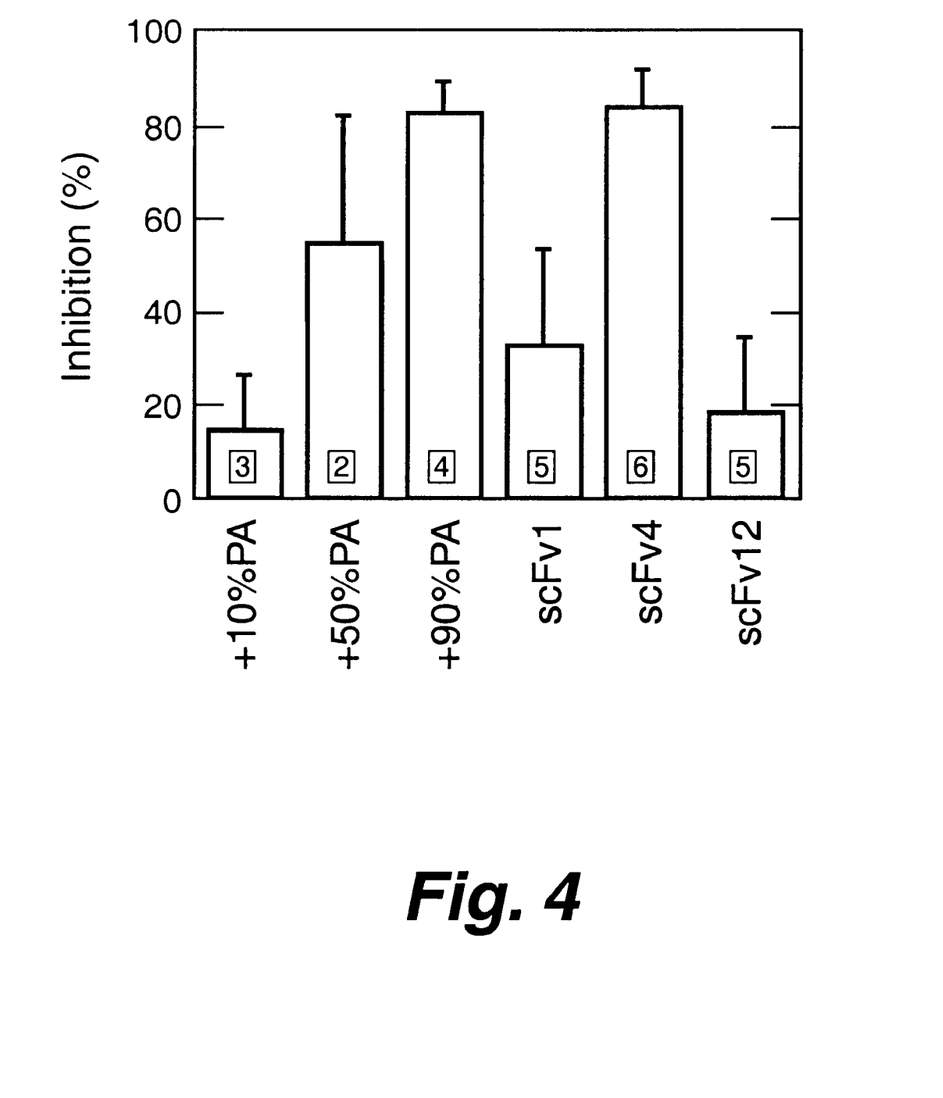
FIG. 4 shows a flow cytometric analysis of the inhibition of EGFP-PA32 mediated fluorescent signal by unlabelled PA molecules (data from FIG. 3) for equimolar concentrations of $scF_v$#1, $scF_v$#4, and $scF_v$#12, where the bars represent the mean and standard error for the indicated number of experiments (boxed numbers).

B. Inhibition of Receptor-mediated EGFP-PA32 Binding by scFv Targeted to PA:

This flow cytometric analysis was subsequently used to screen scFv for their ability to disrupt PA-receptor interactions. Incubation of scFv4 with EGFP-PA32 at a 1:1 molar ratio was able to significantly (>80%) abolish receptor-mediated binding of EGFP-PA32 to A549 cells (FIG. 4). A ten fold molar excess of scFv4 showed little additional inhibition (data not shown) as would be expected for a monovalent competition. The scFv1, which can recognize EGFP-PA32 (FIG. 1), showed minimal inhibition of EGFP-PA32 binding by this assay. This indicates that it does not recognize or mask an essential structure necessary for receptor recognition. The scF$_v$#12 did not inhibit binding as expected since it did not recognize the C-terminal PA32 protein (FIG. 1). For comparison, the means of the dose-dependent competition with unlabeled PA are also shown in FIG. 4. These data indicate the flow cytometric assay is a sensitive and specific method to identify molecules which inhibit receptor-mediated anthrax toxin binding, and that one of the scFv selected has the potential to inhibit PA binding to cells in a therapeutically useful fashion.

PA32 offers several advantages over the current human vaccine. The receptor binding region is a higher proportion of the total immunogenic surface, suggesting a higher proportion of antibodies will be neutralizing. *E. coli* expression and IMAC purification are extremely efficient. Being structurally truncated, the PA32 molecule is unable to interact with toxin A subunits and so is non-toxic, and this PA fragment is unable to form pores due to absence of the D2L2 loop of domain 2.

The current human, *Bacillus anthracis* vaccine used in the United States is an aluminum hydroxide adjuvant conjugated to natural PA83 secreted from a virulent bacteria. Protective effects of this compound, as well as a recombinant, non-toxic PA83 have been tested (See, e.g., B. E. Ivins, et al., Infection and Immunity 60, 662 (1992) and Y. Singh et al., Infection and Immunity 66, 3447 (1998). These vaccines were tested in guinea pigs, the standard model for human anthrax, and it was found that the recombinant PA83, but not the aluminum hydroxide adjuvant/PA83, could protect animals from lethal anthrax infection. This data supports testing of new anthrax vaccines and suggests recombinant PA32 alone or conjugated to novel adjuvants, such as monophosphoryl lipid A (MPL), might be more effective than the current licensed human vaccine.

Anti-PA83 polyclonal antisera from guinea pigs was able to protect non-immunized animals from lethal anthrax challenge (See S. F. Little et al. Infection and Immunity 65, 5171 (1997). Monoclonal antibodies were able to delay time of death but were not protective. This data suggests a combination of the $scF_v$ of the present invention might be effective in protection or treatment of anthrax infection in humans. Delivery of either PA32 or $scF_v$ could be accomplished in two ways: (1) as DNA vaccines such that the host cells (e.g., human epithelial cells) would express the proteins after a delay period; or (2) as purified proteinacious components which are instantly available for therapeutics. DNA immunization is proving very effective in generating host immunity when an immunogen's (e.g., PA32) DNA sequence is injected (See e.g., P. Young, ASM News 63, 659 (1997) and D. M. Klinman et al., J. Immunol 160, 2388 (1998)). Additionally, systems are being developed in which functional scFv can be expressed from DNA vectors in mammalian cells (See, L. Persic et al., Genes 187, 9 (1997)). The uses of purified proteins to compete with PA83 binding (i.e., PA32) or inhibit binding (i.e., $scF_v$) have not been tested.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for screening inhibitors of the toxicity of *Bacillus anthracis*, which comprises the steps of:
   (a) generating the recombinant PA32 DNA fragment, SEQ ID NO. 7, from region 4 of protective antigen PA83 of *Bacillus anthracis* and ligating the PA32 DNA fragment to enhanced green fluorescent protein, EGFP, to form EGFP-PA32;
   (b) expressing the EGFP-PA32 to produce EGFP-PA32 protein;
   (c) contacting the EGFP-PA32 protein with individual cells in a first sample of mammalian cells, thereby generating a first sample of fluorescent cells;
   (d) measuring the fluorescence from individual cells in the first sample of fluorescent cells;
   (e) mixing EGFP-PA32 protein with a potential toxicity inhibitor of *Bacillus anthracis*;
   (f) contacting the mixture of the EGFP-PA32 protein and the potential toxicity inhibitor with individual cells in a second sample of mammalian cells, forming thereby a second sample of fluorescent cells;
   (g) measuring the fluorescence from individual cells in the second sample of fluorescent cells; and
   (h) comparing the fluorescence from individual cells in the first sample of fluorescent cells with the fluorescence from individual cells in the second sample of fluorescent cells, whereby the effectiveness of the toxicity inhibitor is determined from the decrease of the fluorescence from individual cells from the second sample of fluorescent cells relative to the fluorescence from individual cells in the first sample of fluorescent cells.

2. The method for screening inhibitors of the toxicity of *Bacillus anthracis* as described in claim 1, wherein the mammalian cells comprise A549 human bronchial epithelial cells.

3. The method for screening inhibitors of the toxicity of *Bacillus anthracis* as described in claim 1, wherein the fluorescence from individual cells in the first sample of fluorescent cells and from individual cells in the second sample of fluorescent cells is measured using flow cytometry.

* * * * *

SEQUENCE LISTING

<160> NUMBER OF SEQ ID NOS: 12

<210> SEQ ID NO 1
<211> LENGTH: 47
<212> TYPE: DNA
<213> ORGANISM: Bacillus anthracis

<400> SEQUENCE: 1
tcgcactcga gggcgcgcat gccgccgaaa caactgcacg tatcatt          47

<210> SEQ ID NO 2
<211> LENGTH: 54
<212> TYPE: DNA
<213> ORGANISM: Bacillus anthracis

<400> SEQUENCE: 2
actgagctca gcgctagcgc caccagaacc gcctcctatc tcatagcctt tttt    54

<210> SEQ ID NO 3
<211> LENGTH: 23
<212> TYPE: DNA
<213> ORGANISM: Bacillus anthracis

<400> SEQUENCE: 3
gctcgagaat gaacattaca ctg                                   23

<210> SEQ ID NO 4
<211> LENGTH: 29
<212> TYPE: DNA
<213> ORGANISM: Bacillus anthracis

<400> SEQUENCE: 4
cgctcagcac cttctttctt caaactttc                             29

<210> SEQ ID NO 5
<211> LENGTH: 40
<212> TYPE: DNA

<210> SEQ ID NO 6
<211> LENGTH: 39
<212> TYPE: DNA
<213> ORGANISM: Plasmid DNA

<400> SEQUENCE: 5
ggaattccat atggtgagca agggcgagga gctgttcacc            40

<210> SEQ ID NO 6
<211> LENGTH: 39
<212> TYPE: DNA
<213> ORGANISM: Plasmid DNA

<400> SEQUENCE: 6
ccgctcgaga tctgagtact tgtacagctc gtccatgcc            39

<210> SEQ ID NO 7
<211> LENGTH: 867
<212> TYPE: DNA
<213> ORGANISM: Bacillus anthracis

<400> SEQUENCE: 7

```
atgggcagca gccatcatca tcatcatcac agcagcggcc tggtgccgcg cggcagccat       60
atgctcgagg gcgcgcatgc cgccgaaaca actgcacgta tcatttttaa tggaaaagat     120
ttaaatctgg tagaaaggcg gatagcggcg gttaatccta gtgatccatt agaaacgact     180
aaaccggata tgacattaaa agaagccctt aaaatagcat ttggatttaa cgaaccgaat     240
ggaaacttac aatatcaagg aaagacata accgaatttg attttaattt cgatcaacaa     300
acatctcaaa atatcaagaa tcagttagcg gaattaaacg caactaacat atatactgta     360
ttagataaaa tcaaattaaa tgcaaaaatg aatattttaa taagagataa acgttttcat     420
tatgatagaa ataacatagc agttggggcg gatgagtcag tagttaagga ggctcataga     480
gaagtaatta ttcgtcaac agagggatta ttgttaaata ttgataagga tataagaaaa     540
atattatcag gttatattgt agaaattgaa gatactgaag gcttaaagaa gttataaat     600
gacagatatg atatgttgaa tatttctagt ttacggcaag atggaaaaac atttatagat     660
tttaaaaaat ataatgataa attaccgtta tatataagta atcccaatta taggtaaat     720
gtatatgctg ttactaaaga aaacactatt attaatccta gtgagaatgg ggatactagt     780
accaacggga tcaagaaaat tttaatcttt tctaaaaaag gctatgagat aggaggcggt     840
tctggtggcg ctagcgctga gcaataa                                             867
```

<210> SEQ ID NO 8
<211> LENGTH: 288
<212> TYPE: PRT
<213> ORGANISM: Bacillus anthracis

<400> SEQUENCE: 8

Met Gly Ser Ser His His His His His His Ser Ser Gly Leu Val Pro
1               5                   10                  15

Arg Gly Ser His Met Leu Glu Gly Ala His Ala Ala Glu Thr Thr Ala
            20                  25                  30

Arg Ile Ile Phe Asn Gly Lys Asp Leu Asn Leu Val Glu Arg Arg Ile
        35                  40                  45

Ala Ala Val Asn Pro Ser Asp Pro Leu Glu Thr Thr Lys Pro Asp Met
    50                  55                  60

Thr Leu Lys Glu Ala Leu Lys Ile Ala Phe Gly Phe Asn Glu Pro Asn
65                  70                  75                  80

Gly Asn Leu Gln Tyr Gln Gly Lys Asp Ile Thr Glu Phe Asp Phe Asn
                85                  90                  95

```
Phe Asp Gln Gln Thr Ser Gln Asn Ile Lys Asn Gln Leu Ala Glu Leu
                100                 105                 110

Asn Ala Thr Asn Ile Tyr Thr Val Leu Asp Lys Ile Lys Leu Asn Ala
            115                 120                 125

Lys Met Asn Ile Leu Ile Arg Asp Lys Arg Phe His Tyr Asp Arg Asn
        130                 135                 140

Asn Ile Ala Val Gly Ala Asp Glu Ser Val Val Lys Glu Ala His Arg
145                 150                 155                 160

Glu Val Ile Asn Ser Ser Thr Glu Gly Leu Leu Leu Asn Ile Asp Lys
                165                 170                 175

Asp Ile Arg Lys Ile Leu Ser Gly Tyr Ile Val Glu Ile Glu Asp Thr
            180                 185                 190

Glu Gly Leu Lys Glu Val Ile Asn Asp Arg Tyr Asp Met Leu Asn Ile
        195                 200                 205

Ser Ser Leu Arg Gln Asp Gly Lys Thr Phe Ile Asp Phe Lys Lys Tyr
        210                 215                 220

Asn Asp Lys Leu Pro Leu Tyr Ile Ser Asn Pro Asn Tyr Lys Val Asn
225                 230                 235                 240

Val Tyr Ala Val Thr Lys Glu Asn Thr Ile Ile Asn Pro Ser Glu Asn
                245                 250                 255

Gly Asp Thr Ser Thr Asn Gly Ile Lys Lys Ile Leu Ile Phe Ser Lys
                260                 265                 270

Lys Gly Tyr Glu Ile Gly Gly Gly Ser Gly Gly Ala Ser Ala Glu Gln
            275                 280                 285

<210> SEQ ID NO 9
<211> LENGTH: 908
<212> TYPE: DNA
<213> ORGANISM: Homo sapiens

<400> SEQUENCE: 9
cttgcatgca aattctattt caaggagaca gtcataatga ataccctatt gcctacggca        60
gccgctggat tgttattact cgcggcccag ccggccatgg cccaggtcaa cttaagggag       120
tctgggggag gcttggtaca gcctgggggg tccctgagac tctcctgtgc agcctctgga       180
ttcaccttca gcagctatgc catgagctgg gtccgccagg ctccagggaa ggggctggag       240
tgggtctcag ctattagtag taatggggt agtacatact acgcagactc agtgaagggc        300
agattcacca tctccagaga caattccaag aacacgctgt atcttcaaat gagcagtctg       360
agagctgagg acacggccct gtattactgt gcgagagaga gggggcggc agcagcctct        420
gactactggg gcccgggaac cctggtcacc gtctcctcag gtggaggcgg ttcaagcgga       480
ggtggctctg gcggtggcgg atcgcagtct gtgttgacgc aaccgccctc agcgtctggg       540
acccccgggc agagggtcac catctcttgt tctggaagca gctccaacat cggaagtaat       600
tctgttaact ggtaccagca gctcccagga acggcccca aactcctcat ctatagtaac       660
agcaatcggc cctcagggt ccctgaccga ttctctggct ccaagtctgg cacctcagcc        720
tccctggcca tcagtgggct ccggtccgag gatgaggctg attattactg tgcagcatgg       780
gatgacagcc tgagtggtcg ggtgttcggc ggagggacca agctgaccgt cctaggtgcg       840
gccgcagaac aaaaactcat ctcagaagag gatctgaatg gggccgcaca tcaccatcat       900
caccatta                                                                908

<210> SEQ ID NO 10
```

<211> LENGTH: 913
<212> TYPE: DNA
<213> ORGANISM: Homo sapiens

<400> SEQUENCE: 10

| | | | | | |
|---|---|---|---|---|---|
| cttgcatgca | aattctattt | caaggagaca | gtcataatga | aatacctatt | gcctacggca | 60 |
| gccgctggat | tgttattact | cgcggcccag | ccggccatgg | cccaggtgca | gctggtggag | 120 |
| tctgggggag | gcttggtcca | gcctgggggg | tccctgagac | tctcctgttc | agcctctgga | 180 |
| ttcaccttca | gtagctatgc | tatgcactgg | gtccgccagg | ctccagggaa | gggactggaa | 240 |
| tatgtttcag | ctattagtag | taatgggggt | agcacatact | acgcagactc | cgtgaagggc | 300 |
| agattcacca | tctccagaga | caattccaag | aacacgctgt | atcttcaaat | gagcagtcta | 360 |
| agagctgagg | acacggctgt | gtattactgt | gtgaaagatc | tccacgttgg | acggctacaa | 420 |
| ttggggtat | ttgactactg | gggccaggc | accctggtca | ccgtctcctc | aggtggaggc | 480 |
| ggttcaggcg | gaggtggctc | tggcggtggc | ggatcgtctg | agctgactca | ggaccctgct | 540 |
| gtgtctgtgg | ccttgggaca | gacagtcaga | atcacatgcc | aaggagacag | cctcagaagc | 600 |
| tattatgcaa | gctggtacca | gcagaagcca | ggacaggccc | ctgtacttgt | catctatggt | 660 |
| aaaaacaacc | ggccctcagg | gatcccagac | cgattctctg | gctccagctc | aggaaacaca | 720 |
| gcttccttga | ccatcactgg | ggctcaggcg | gaagatgagg | ctgactatta | ctgtaactcc | 780 |
| cgggacagca | gtagtaccca | tcgagggggtg | ttcggcggag | ggaccaagct | gaccgtccta | 840 |
| ggtgcggccg | cagaacaaaa | actcatctca | gaagaggatc | tgaatggggc | cgcacatcac | 900 |
| catcatcacc | ata | | | | | 913 |

<210> SEQ ID NO 11
<211> LENGTH: 892
<212> TYPE: DNA
<213> ORGANISM: Homo sapiens

<400> SEQUENCE: 11

| | | | | | |
|---|---|---|---|---|---|
| cttgcatgca | aattctattt | caaggagaca | gtcataatga | aatacctatt | gcctacggca | 60 |
| gccgctggat | tgttattact | cgcggcccag | ccggccatgg | cccaggtgca | gctggtggag | 120 |
| tctgggggag | gcgtggtcca | gcctgggagg | tccctgagac | tctcctgtgc | agcctctgga | 180 |
| ttcaccttca | ataaccatgc | tatggaatgg | gtccgccagg | ctccaggcaa | ggggctggag | 240 |
| tgggtctctg | gtattaattg | gatggtggt | agcacaggtt | atgcagactc | tgtgaagggc | 300 |
| cgattcgccg | tctccagaga | caacgccaag | aactccctgt | atctgcaaat | aaacagtctg | 360 |
| agagacgagg | acacggctgt | gtattactgt | gccagagcta | actggggacg | cattgactac | 420 |
| tggggccagg | gcaccctggt | caccgtctcc | tcaggtggag | gcggttcagg | cggaggtggc | 480 |
| tctggcggtg | gcggatcgtc | tgagctgact | caggaccctg | ctgtgtctgt | ggccttggga | 540 |
| cagacagtca | ggatcacatg | ccaaggagac | agtctcagaa | ggtattatgc | aagctggtac | 600 |
| cagcagaagc | caggacaggc | ccctgtactt | gtcatctatg | gtaaaaacaa | ccggccctca | 660 |
| gggatcccag | accgattctc | tggctccagc | tcaggaaaca | cagcttcctt | gaccatcact | 720 |
| ggggctcagg | cggaagatga | ggctgactat | tactgtcact | cccgggacag | cagtggtacc | 780 |
| catctaaggg | tattcggcgg | agggaccaag | ctgaccgtcc | taggtgcggc | cgcagaacaa | 840 |
| aaactcatct | cagaagagga | tctgaatggg | gccgcacatc | accatcatca | cc | 892 |

<210> SEQ ID NO 12
<211> LENGTH: 903

-continued

```
<212> TYPE: DNA
<213> ORGANISM: Homo sapiens

<400> SEQUENCE: 12
cttgctgcaa attctatttc aaggagacag tcataatgaa atacctattg cctacggcag      60
ccgctggatt gttattactc gcggcccagc cggccatggc ccaggtgcag ctggtggagt     120
ctgggggagg cttggtccag cctgggggt ccctgagact ctcctgttca gcctctggat     180
tcaccttcag tagctatgct atgcactggg tccgccaggc tccagggaag ggactggaat    240
atgtttcagc tattagtagt aatggggta gcacatacta cgcagactcc gtgaagggca     300
gattcaccat ctccagagac aattccaaga acacgctgta tcttcaaatg agcagtctaa    360
gagctgagga cacggctgtg tattactgtg tgaaagatct ccacgttgga cggctacaat    420
tgggggtatt tgactactgg ggccagggaa ccctggtcac cgtctcctca ggtggaggcg    480
gttcaggcgg aggtggctct ggcggtggcg gatcgtctga gctgactcag gaccctgctg    540
tgtctgtggc cgtgggacag acagtcaaga tcacatgcca aggagacagc ctcagaagct    600
attatgcaac ctggtaccag cagaagccag gacaggcccc tgttcttgtc atctatggta    660
aaaacagccg gccctcaggg atcccagacc gattctctgg gtccagctca ggaaccacag    720
cttcctttac catcactggg gctcaggcgg aagatgaggc tgactattac tgtaattccc    780
gggacagtac taataatcag ctgttcggcg gagggaccaa gctgaccgtc ctaggtgcgg    840
ccgcagaaca aaaactcatc tcagaagagg atctgaatgg ggccgcacat caccatcatc    900
acc                                                                   903
```